(12) United States Patent
Hatanaka (10) Patent No.: US 10,856,863 B2
(45) Date of Patent: Dec. 8, 2020

(54) THREAD FIXING TOOL, ENDOSCOPE SYSTEM AND METHOD FOR FIXING SUTURE THREAD

(71) Applicant: OLYMPUS CORPORATION, Tokyo (JP)

(72) Inventor: Takayuki Hatanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 122 days.

(21) Appl. No.: 16/142,202

(22) Filed: Sep. 26, 2018

(65) Prior Publication Data

US 2019/0021725 A1 Jan. 24, 2019

Related U.S. Application Data

(63) Continuation of application No. PCT/JP2016/060341, filed on Mar. 30, 2016.

(51) Int. Cl.
*A61B 17/04* (2006.01)
*A61B 1/005* (2006.01)
(Continued)

(52) U.S. Cl.
CPC .......... *A61B 17/0487* (2013.01); *A61B 1/005* (2013.01); *A61B 1/018* (2013.01); *A61B 17/0469* (2013.01); *A61B 17/0482* (2013.01); *A61B 2017/00292* (2013.01); *A61B 2017/0488* (2013.01)

(58) Field of Classification Search
CPC ............ A61B 17/04; A61B 2017/0488; A61B 2017/00292; A61B 2017/0487; A61B 17/0482; A61B 17/0469; A61B 1/018; A61B 1/005
See application file for complete search history.

(56) References Cited

U.S. PATENT DOCUMENTS

| 5,902,321 A * | 5/1999 | Caspari .............. A61B 17/0487 606/232 |
| 2010/0318125 A1 | 12/2010 | Gerber et al. |
| 2011/0264140 A1 | 10/2011 | Lizardi et al. |

FOREIGN PATENT DOCUMENTS

| EP | 2319428 A1 * | 5/2011 | ......... A61B 17/0487 |
| JP | H10-509612 A | 9/1998 | |

(Continued)

OTHER PUBLICATIONS

International Search Report dated Jun. 21, 2016 issued in PCT/JP2016/060341.

*Primary Examiner* — George J Ulsh
(74) *Attorney, Agent, or Firm* — Scully, Scott, Murphy & Presser, P.C.

(57) ABSTRACT

The first fixing member and the second fixing member are arranged such that the first clamping surface and the second clamping surface face each other in an axis line direction of the insertion portion. When the manipulation portion is manipulated and the insertion portion and manipulation member is rotated relatively, the first clamping surface and the second clamping surface are configured to approach by screw-fitting with the second fixing member and the first fixing member. When a predetermined manipulation is performed to the manipulation portion, a coupling between the manipulation member and the other is configured to be released.

9 Claims, 8 Drawing Sheets

(51) Int. Cl.
*A61B 1/018* (2006.01)
*A61B 17/00* (2006.01)

(56) References Cited

FOREIGN PATENT DOCUMENTS

| | | | |
|---|---|---|---|
| JP | 2001-502190 | A | 2/2001 |
| JP | 2005-504555 | A | 2/2005 |
| JP | 2008-501428 | A | 1/2008 |
| JP | 2010-508119 | A | 3/2010 |
| JP | 2011-092742 | A | 5/2011 |
| JP | 2011-524238 | A | 9/2011 |
| WO | WO 96/14798 | A1 | 5/1996 |
| WO | WO 97/30639 | A1 | 8/1997 |
| WO | WO 02/43576 | A2 | 6/2002 |
| WO | WO 2006/060035 | A2 | 6/2006 |
| WO | WO 2008/054814 | A2 | 5/2008 |
| WO | WO 2009/155287 | A1 | 12/2009 |
| WO | WO 2015/134872 | A1 | 9/2015 |

* cited by examiner

THREAD FIXING TOOL, ENDOSCOPE SYSTEM AND METHOD FOR FIXING SUTURE THREAD

This application is a continuation application based on a PCT Patent Application No. PCT/JP2016/060341, filed on Mar. 30, 2016. The content of the PCT Application is incorporated herein by reference.

TECHNICAL FIELD

The present invention relates to a thread fixing tool for medical use that holds a suture state of a suture thread penetrated through a tissue.

BACKGROUND ART

Conventionally, various treatments are performed using a flexible endoscope inserted into a hollow organ of a gastrointestinal tract or the like. Generally, these treatments are performed to insert a treatment tool of the endoscope and to cause a distal end of the treatment tool to be protruded from an insertion portion of the endoscope.

One of the difficulty treatments is a suture using a suture thread. A series of procedures of the suture include an action in which the suture thread is penetrated through the tissue and an action in which a knot is formed in the suture thread such that the suture thread penetrated through the tissue continues to apply a predetermined tension to the tissue. The more difficult procedure is the later and it is not easy to form the knot using the treatment tool.

Instead of making the knot, the suture collet that is capable of fixing the suture thread by inserting the sure thread into an outside member and by a screw fitting an inside member into the outside member is suggested (for example, Japanese Translation of PCT International Application Publication No. 2001-502190).

SUMMARY OF THE INVENTION

The present invention includes: a first fixing member which has a screw hole and a first clamping surface; a second fixing member which has a second clamping surface and screw-fits with the first fixing member; an insertion portion which is flexible and tubular, either one of the first fixing member and the second fixing member being attached to a distal end portion of the insertion portion; a manipulation member which is inserted into the insertion portion and to which the other one of the first fixing member and the second fixing member is coupled; and a manipulation portion which is connected to a proximal end portion of the manipulation member. The first fixing member and the second fixing member are arranged such that the first clamping surface and the second clamping surface face each other in an axis line direction of the insertion portion. When the insertion portion rotates relative to the manipulation member by manipulating the manipulation portion, the first clamping surface and the second clamping surface are configured to be close to each other by screw-fitting with the second fixing member and the first fixing member. When a predetermined manipulation is performed to the manipulation portion, a coupling between the manipulation member and the other one of the first fixing member and the second fixing member is configured to be released. The manipulation member and the other one of the first fixing member and the second fixing member are configured to be coupled such that the coupling is capable of being released by causing the coupling holding member to be retracted with respect to the manipulation member.

One of the first fixing member and the second fixing member may be attached to the insertion portion so as to be capable of moving relative to the insertion portion in the axis line direction and so as not to rotate around the axis line relative to the insertion portion.

The thread fixing tool of the present invention may further include a coupling holding member which is arranged in the insertion portion and into which the manipulation member is inserted. A coupling between the manipulation member and the other one of the first fixing member and the second fixing member may be configured to be capable of being released by causing the coupling holding member to be retracted with respect to the manipulation member.

The predetermined manipulation may be a manipulation in which the manipulation member is retracted with respect to the insertion portion.

The predetermined manipulation may be a manipulation in which the manipulation member is rotated relative to the insertion portion.

The manipulation member and the other one of the first fixing member and the second fixing member may be coupled via a fragility portion, and the fragility portion is configured to be broken by the predetermined manipulation.

The first clamping surface and the second clamping surface may be orthogonal to an axis line of the insertion portion.

The thread fixing tool may further include a wall portion which is provided in a proximal end portion of one of the first fixing member and the second fixing member. The wall portion may be capable of being detached from and attached to a coupling chip that is provided in a distal end of the manipulation member.

An endoscope system includes: an endoscope which includes an insertion portion that is flexible; and the thread fixing tool according to claim 1 which is attached along an outer peripheral portion of the insertion portion of the endoscope. The first fixing member and the second fixing member are protruded from a distal end side of the endoscope than a distal end of the insertion portion.

A method for fixing a suture thread using the thread fixing tool according to the above, the method includes: entering the suture thread between the first fixing member and the second fixing member; causing the first fixing member and the second fixing member to be close to each other by screw-fitting with the second fixing member and the first fixing member, and clamping and fixing the suture thread; releasing the coupling by causing the coupling holding member to be retracted with respect to the manipulation member; and leaving the first fixing member and the second fixing member in a state of cramping and fixing the suture thread in a body.

DESCRIPTION OF EMBODIMENTS

First Embodiment

Figure 1:
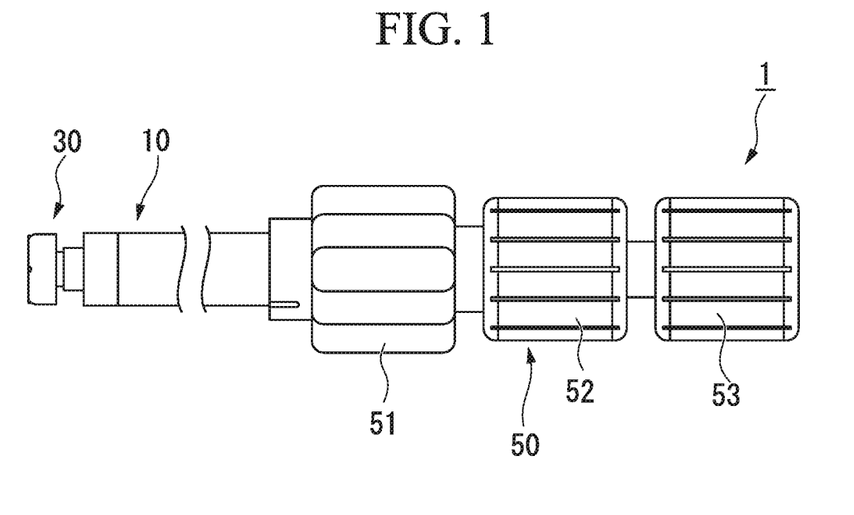
FIG. 1 is a view showing a thread fixing tool of a first embodiment of the present invention.
Figure 2:
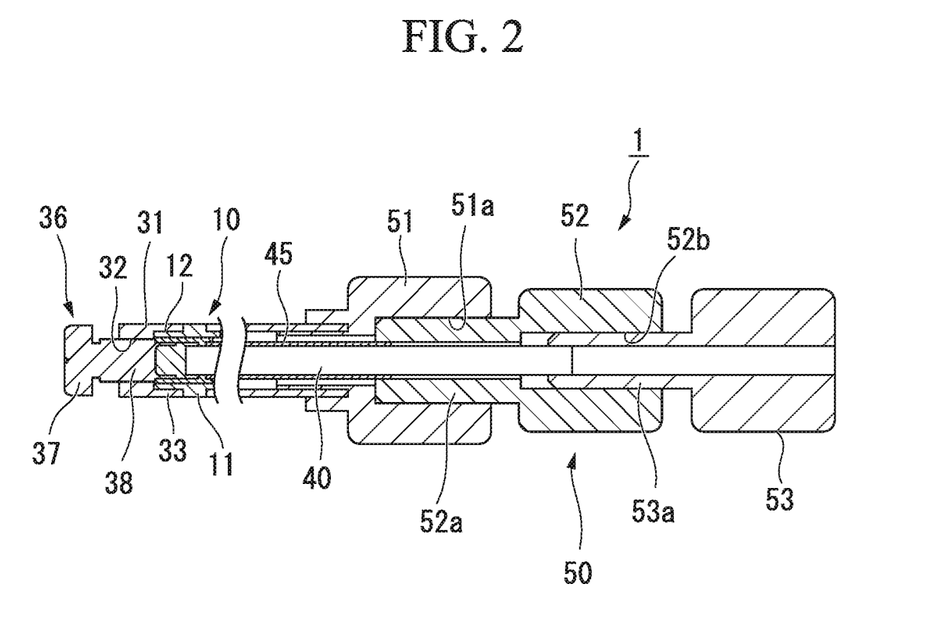
FIG. 2 is a cross-sectional view of the thread fixing tool.

A first embodiment of the present invention will be described with reference to FIGS. 1 to 9D. FIG. 1 is a view showing a thread fixing tool 1 of a first embodiment of the present invention. FIG. 2 is a cross-sectional view of the thread fixing tool 1. As shown in FIG. 1, a thread fixing tool 1 includes an insertion portion 10, a fixing portion 30 that is attached to a distal end of the insertion portion 10, and a manipulation portion 50 that is provided at a proximal end of the insertion portion 10.

The side at which the fixing portion 30 is provided is referred to as a distal end side of the thread fixing tool 1 and the side at which the manipulation portion 50 is provided is referred to as a proximal end side of the thread fixing tool 1.

The insertion portion 10 is preferably tubular and flexible, e.g., a coil sheath. In a case of forming by the coil sheath, a multilayer coil may be used from an aspect of torque transmission.

The dimensions of each portion of the insertion portion 10 can be set appropriately. For example, the length in which the insertion portion 10 is inserted into a treatment tool channel and is protruded from the treatment tool channel can be determined.

As shown in FIG. 2, a distal end member 11 that is a ring shape is attached to a distal end of the insertion portion 10.

The fixing portion 30 includes a nut portion (first fixing member) 31 that is attached to the distal end portion of the insertion portion 10 and a bolt portion (second fixing member) 36 that is arranged in front of the nut portion 31.

The nut portion 31 is formed of metal and is a ring shape, as shown in FIG. 2, a screw groove (not shown) is formed in an inner surface of the screw hole 32. In a proximal end side of the nut portion 31, an engaging portion 33 extends and the engaging portion 33 is arranged in an engaged portion 12 formed in the distal end member 11, thereby the nut portion 31 is attached to the insertion portion 10. The nut portion 31 is attached so as not to be capable of rotating around an axis line of the insertion portion 10 relative to the distal end member 11 and to be capable of being separated from the distal end member 11 by engaging the engaging portion 33 and the engaged portion 12.

The bolt portion 36 includes a disk portion 37 that has a substantially disk shape and a screw portion 38 that has a columnar shape and extends from the disk portion 37. A screw thread (not shown) that is capable of fitting with the screw groove of the nut portion 31 is formed in an outer periphery surface of the screw portion 38. A dimension in the axis line direction of the screw portion 38 is longer than the screw hole 32. The bolt portion 36 is arranged such that the screw portion 38 screw-fits with the screw hole 32 and the screw portion 38 is protruded to both sides of the axis line direction of the nut portion 31.

Figure 3:
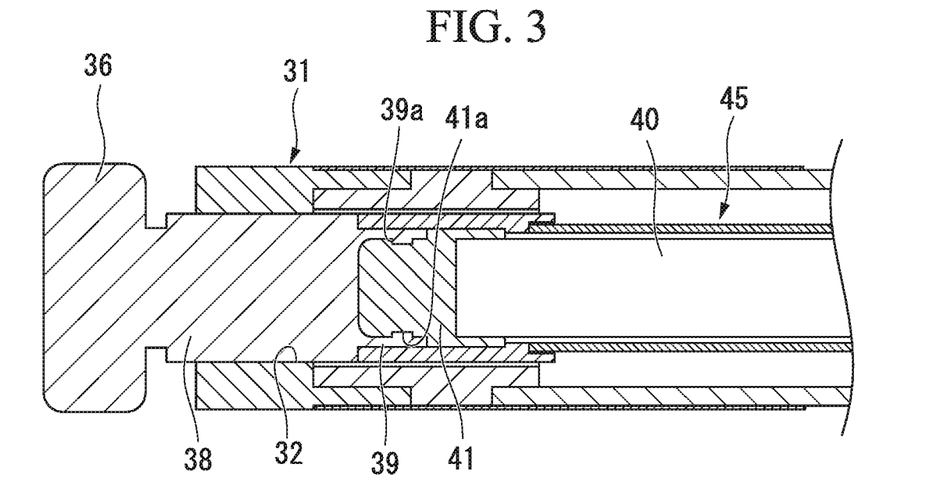
FIG. 3 is an enlarged cross-sectional view of a distal end portion of the thread fixing tool.

FIG. 3 is an enlarged cross-sectional view of a distal end portion of the thread fixing tool 1. As shown in FIG. 3, a distal end portion of the screw portion 38 protruded to a proximal end side of the nut portion 31 includes a pair of wall portions 39. Each pair of wall portions 39 includes convex portions 39a protruded to the inner surface.

A manipulation wire (manipulation member) 40 that is connected to the bolt portion 36 and the manipulation portion 50 is arranged in the insertion portion 10. A coupling chip 41 that is coupled to the screw portion 38 is connected to a distal end portion of the manipulation wire 40. As shown in FIG. 3, a concave portion 41a that corresponds to the convex portion 39a in an outer periphery surface of the coupling chip 41. The bolt portion 36 and the manipulation wire 40 are coupled by engaging the convex portion 39a and the concave portion 41a.

A control sheath (coupling holding member) 45 is arranged between the manipulation wire 40 and the insertion portion 10. The control sheath 45 is capable of being advanced and retracted with respect to the insertion portion 10 and the manipulation wire 40 relatively. In a state of an initial state of the thread fixing tool 1 shown in FIG. 3, a distal end portion of the control sheath 45 covers an engaging part between the convex portion 39a and the concave portion 41a.

As shown in FIGS. 1 and 2, the manipulation portion 50 includes a first knob 51 that is connected to the insertion portion 10, a second knob 52 that is attached to a proximal end side of the first knob 51, and a third knob 53 that is attached to a proximal end side of the second knob 52.

An engaging hole 51a is formed in the proximal end side of the first knob 51. A screw groove (not shown) that has a pitch equal to that of the screw groove of the screw hole 32 is formed in part of an inner surface of the engaging hole 51a.

A screw thread (not shown) is formed in part of an outer surface of a distal end portion 52a of the second knob 52. The distal end portion 52a screw-fits with the engaging hole 51a and enters into the engaging hole 51a. A proximal end portion of the control sheath 45 is connected to the distal end portion 52a of the second knob 52.

A distal end portion 53a of the third knob 53 enters into a slide hole 52b that is formed in the proximal end side of the second knob 52. A cross-section shape perpendicular to a longitudinal direction of the thread fixing tool 1 of the slide hole 52b and the distal end portion 53a is polygonal or a non-circular of D shape or the like. Thereby, the third knob 53 is capable of moving relative to the second knob 52 in the longitudinal direction and is not capable of rotating around the longitudinal axis. A proximal end portion of the manipulation wire 40 is connected to the distal end portion 53a of the third knob 53.

The movement when using the thread fixing tool 1 that is configured as described above will be described.

Before using the thread fixing tool 1, the operator catches the suture thread on the tissue of a target under the endoscope. A procedure catching the suture thread on the tissue can be performed using various suture devices that are capable of being used in combination with the endoscope.

Figure 4:
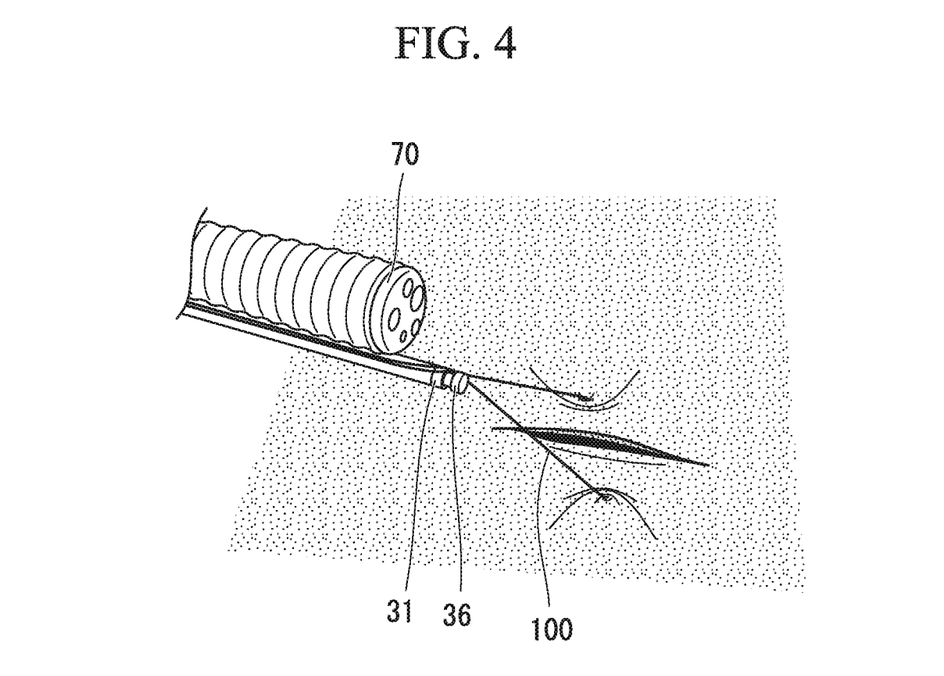
FIG. 4 is a view showing a part of process when using the thread fixing tool.

Next, the operator introduces the thread fixing tool 1 from the distal end side of the thread fixing tool 1 into a body of a patient and moves the fixing portion 30 in a vicinity of the suture thread. The thread fixing tool 1 may be introduced via the treatment tool channel or may be introduced via an external channel that is parallel to the endoscope. The thread fixing tool 1 may be attached along the insertion portion of the endoscope using a band or the like and, as shown in FIG. 4, the thread fixing tool 1 may be introduced with the endoscope 70 in advance.

The operator applies a predetermined tension to the suture thread 100 and the operator enters the suture thread 100 in which the operator wants to fix between the bolt portion 36 and the nut portion 31. This procedure may be performed using, for example, a grasping forceps that is introduced into the body separately.

While holding a state where part of the suture thread 100 enters between the bolt portion 36 and the nut portion 31, the first knob 51 and the second knob 52 are rotated in a predetermined direction relatively by the operator and a helper ((hereinafter, simply referred to as a "operator or the like"). The manipulation wire 40 that is integral with the control sheath 45 rotates in a direction same as the rotation direction of the second knob 52. As a result, while the screw portion 38 screw-fits with the screw hole 32 of the nut portion 31, the bolt portion 36 moves to the proximal end side and approach the nut portion 31. Because the screw thread of the second knob 52 and the screw thread of the screw portion 38 have the same pitch, a synchronization between a rotating operation of the second knob 52 and a rotating operation of the bolt portion 36 is ensured and the bolt portion 36 moves suitably.

As described above, when the first knob 51 rotates relative to the second knob 52, the nut portion 31 does not rotate with respect to the distal end member 11 and the manipulation wire 40 does not rotate with respect to the second knob 52 because the nut portion 31 cannot rotate relative to the distal end member 11 and the second knob 52 cannot rotate relative to the third knob 53. Accordingly, the bolt portion 36 suitably rotates relative to the nut portion 31, the bolt portion 36 retracts with respect to the nut portion 31, and an end surface (first clamping surface) 31a (see FIG. 5) of the distal end side of the nut portion 31 and a surface (second clamping surface) 37a (see FIG. 5) of the proximal end side of the disk portion 37 of the bolt portion 36 approach each other. When the insertion portion 10 rotates relative to the manipulation wire 40 by manipulating the manipulation wire 40, the end surface 31a and the surface 37a are configured to be close to each other by screw-fitting with the nut portion 31 and the bolt portion 36.

Figure 5:
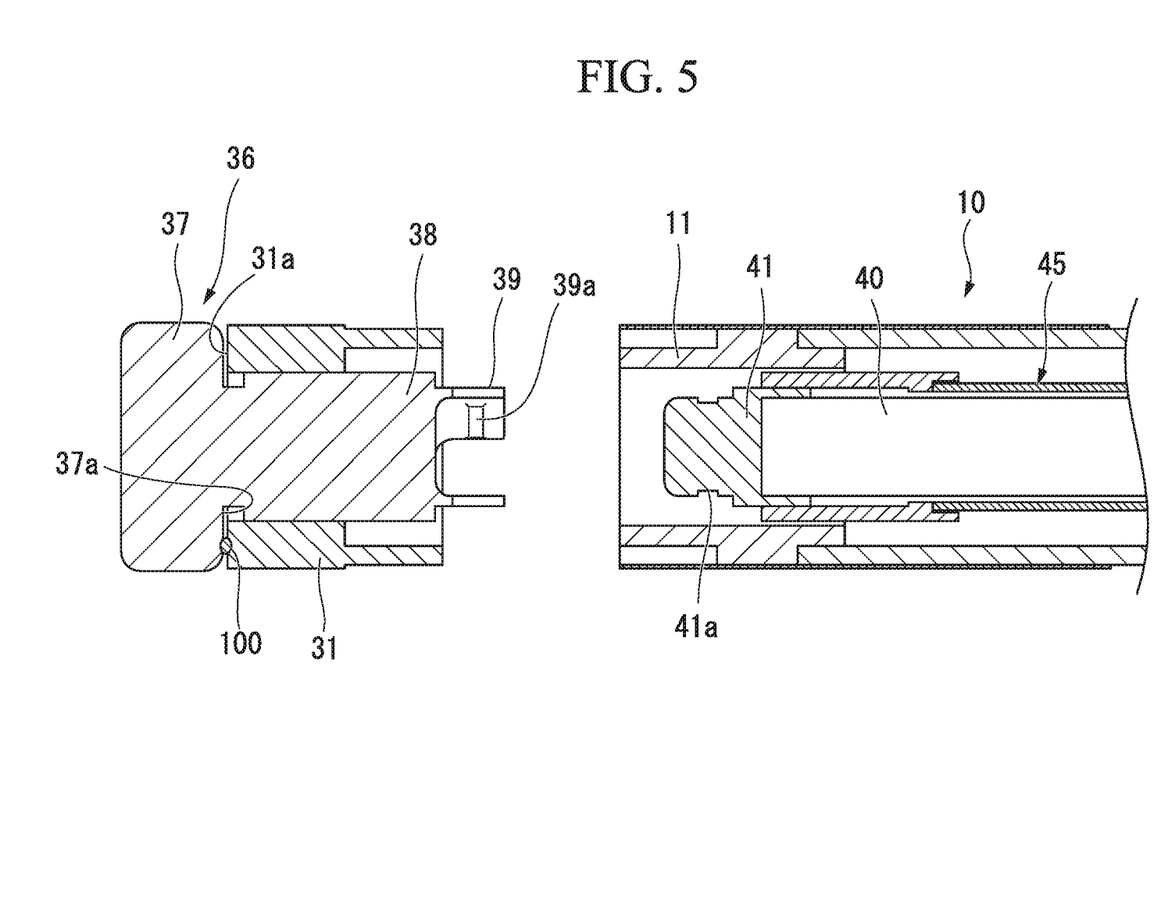
FIG. 5 is an enlarged cross-sectional view showing a part of process when using the thread fixing tool.

As the bolt portion 36 and the nut portion 31 further approach, the suture thread 100, as shown in FIG. 5, is clamped between the first clamping surface 31a and the second clamping surface 37a orthogonal to the axis line of the insertion portion 10 and is tightened. When the suture thread 100 that is clamped between the first clamping surface 31a and the second clamping surface 37a, the suture thread 100 that is penetrated through the tissue is fixed so as not to loosen by the fixing portion 30.

The operator or the like removes the fixing member 30 from the insertion portion 10 after the suture thread 100 is fixed sufficiently by the fixing portion 30. When removing the fixing member 30, the operator or the like rotates the second knob 52 with respect to the first knob 51 and the screw fitting between the first knob 51 and the second knob 52 is released. After that, the operator manipulates the second knob 52 so as to retract with respect to the first knob 51 and the third knob 53, as shown in FIG. 5, the control sheath 45 is retracted with respect to the insertion portion 10 and the manipulation wire 40. When the control sheath 45 is retracted, a coupling portion between the bolt portion 36 and the manipulation wire 40 is not covered by the control sheath 45. As a result, the wall portion 39 of the bolt portion 36 is capable of deforming radially outward.

In this state, when the operator causes the third knob 53 to be retracted with respect to the first knob 51, an engagement between the convex portion 39a and the concave portion 41a is released, as shown in FIG. 5, the bolt portion 36 and the manipulation wire 40 are separated. Furthermore, when the insertion portion 10 is retracted, the nut portion 31 is released from the distal end member 11. As a result, the fixing portion 30 is removed from the insertion portion 10 in the state where the fixing portion 30 fixes the suture thread 100 and is left in the body.

As described above, according to the thread fixing tool 1 of the present embodiment, the suture thread 100 is entered between the first clamping surface 31a of the nut portion 31 and the second clamping surface 37a of the bolt portion 36 and the suture thread 100 is fixed by the first clamping surface 31a and the second clamping surface 37a. The suture thread is entered easily because the first clamping surface 31a and the second clamping surface 37a that are arranged to be opposed to each other in the distal end of the insertion portion 10 are orthogonal to the axis line of the insertion portion 10. Therefore, the fixing of the suture thread is performed very easily compared to entering the suture thread into the screw hole of the conventional technology.

In the thread fixing tool 1, the fixing can be performed with sufficient competence by tightening the tissue appropriately regardless of the diameter of the suture thread that is clamped and fixed because the distance between the first clamping surface 31a and the second clamping surface 37a is capable of adjusting continuously to substantively zero.

Furthermore, in the state of an initial state of the thread fixing tool 1, the coupling portion between the bolt portion 36 and the manipulation wire 40 is protected by the control sheath 45. Accordingly, a condition in which the coupling between the bolt portion 36 and the manipulation wire 40 comes off unintentionally is prevented suitably until the suture thread 100 is fixed, and after fixing, the coupling between the bolt portion 36 and the manipulation wire 40 can be released easily and can remove the fixing portion 30 from the insertion portion 10 easily by retracting the control sheath 45 and moving away.

In the present embodiment, a configuration in which the coupling between the second fixing member and the manipulation member after fixing the suture thread is capable of releasing is not limited by using the above control sheath 45.

Another example of the configuration of the coupling portion will be described below.

Figure 6A:
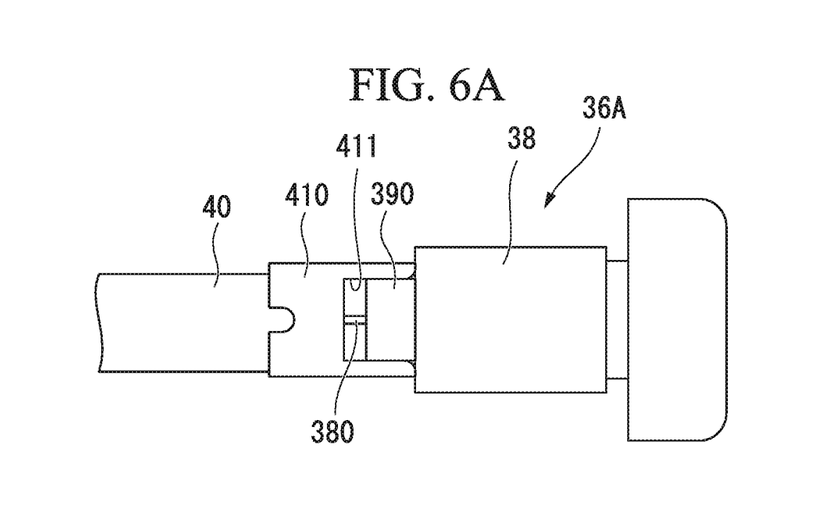
FIG. 6A is a view showing a bolt portion and a manipulation wire of the modified example of the thread fixing tool.
Figure 6B:
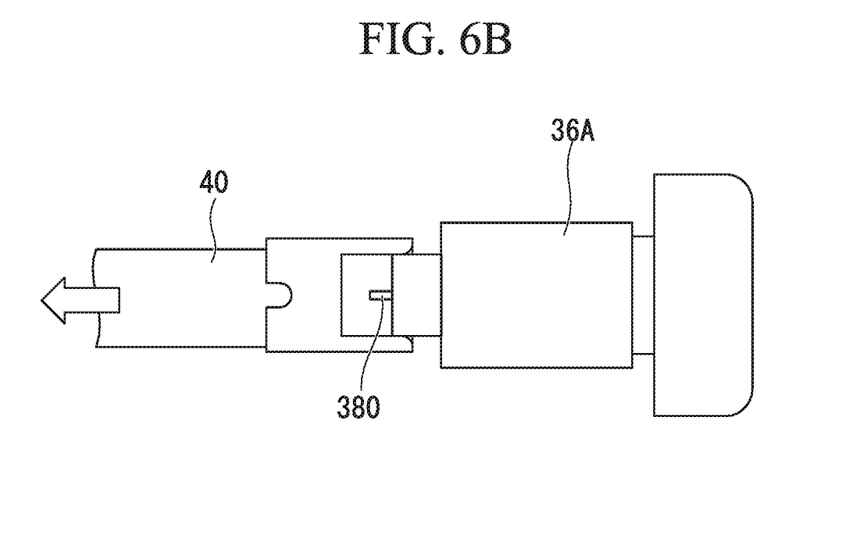
FIG. 6B is a view showing the bolt portion and the manipulation wire of the modified example of the thread fixing tool.

FIGS. 6A and 6B are views showing a bolt portion 36A and the manipulation wire 40 of a modified example of the present embodiment. As shown in FIG. 6A, the convex portion 39a is not provided in a pair of wall portions 390 of the bolt portion 36 and a notch 411 in which the wall portions 390 is capable of entering is formed in a distal end tip 410 that is attached to the manipulation wire 40 instead of the concave portion 41a. A fragility portion 380 that in which a dimension of a radial direction is smaller than the manipulation wire 40 and the screw portion 38 is provided in the distal end of the manipulation wire 40. The bolt portion 36A and the manipulation wire 40 are coupled by bonding the fragility portion 380 with the screw portion 38 and welding.

In the present modified example, when the coupling between the bolt portion 36A and the manipulation wire 40 is released after fixing the suture thread, the third knob 53 is retracted. When a predetermined force is applied to the fragility portion 380 by the retract of the manipulation wire 40, as shown in FIG. 6, the fragility portion 380 is broken and the bolt portion 36A is removed from the manipulation wire 40.

In the present modified example, because it is not necessary to provide the control sheath 45, it is not necessary to provide a configuration for moving the control sheath in the manipulation portion.

In the present modified example, a shape of the fragility portion may be a liner shape, a plate shape, or the like, and may be suitably set in consideration of the amount of force required for broken.

Figure 7A:
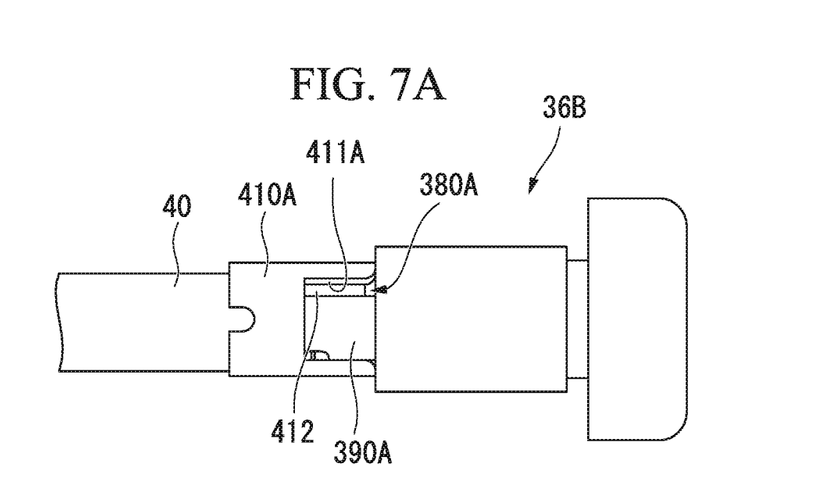
FIG. 7A is a view showing a bolt portion and a manipulation wire of the modified example of the thread fixing tool.
Figure 7B:
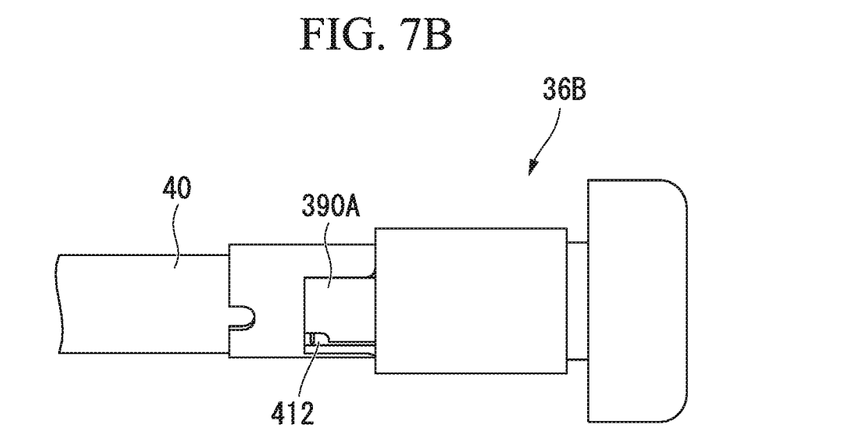
FIG. 7B is a view showing the bolt portion and the manipulation wire of the modified example of the thread fixing tool.

Another example of the fragility portion will be described in FIGS. 7A and 7B. As shown in FIG. 7A, a dimension of a circumferential direction of a notch 411A that is formed in a distal end tip 410A is set larger than a dimension of a circumferential direction of a wall portion 390A of a bolt portion 36B and the notch 411A is formed so as to include a bottom surface 412. The wall portion 390A that enters into the notch 411A contacts to the bottom surface 412 by a bond or the like. That is, in the present modified example, a connecting portion between the wall portion 390A and the bottom surface 412 serves as a fragility portion 380A.

Because the bolt portion 36B and the manipulation wire 40 are coupled so as not to rotate relatively by the fragility portion 380A, when the bolt portion 36B and the nut portion 31 are capable of approaching, the bolt portion 36B and the manipulation wire 40 rotate integrally. After the bolt portion 36B and the nut portion 31 sufficiently approach and cannot move relatively, furthermore when the manipulation wire 40 attempts to rotate, the force is applied to the fragility portion 380A by the rotating manipulation. When the applied force equals to a predetermined value or greater, the fragility portion 380A is broken, as shown in FIG. 7B, the wall portion 390A moves relative to the bottom surface 412 and the coupling between the bolt portion 36B and the manipulation wire 40 is released. After releasing the coupling, because the bolt portion 36B and the manipulation wire 40 are separated by retracting the insertion portion 10, it is not necessary to include a configuration in which the third knob is provided in the manipulation portion and is capable of retracting the manipulation wire 40 with respect to the insertion portion 10.

Figure 8A:
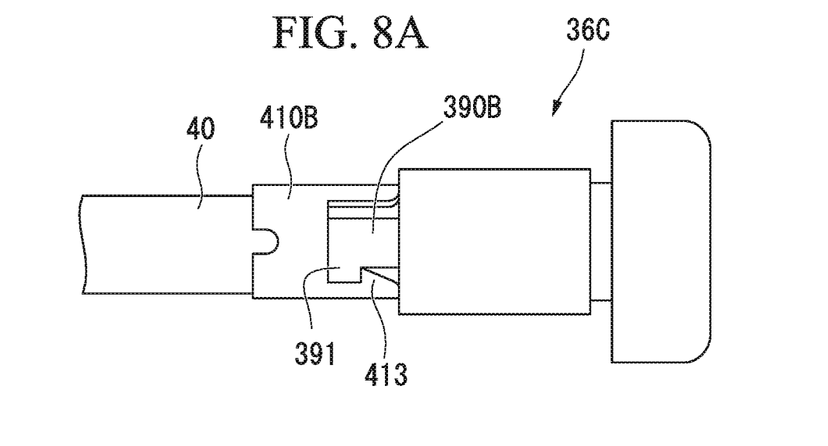
FIG. 8A is a view showing a bolt portion and a manipulation wire of the modified example of the thread fixing tool.
Figure 8B:
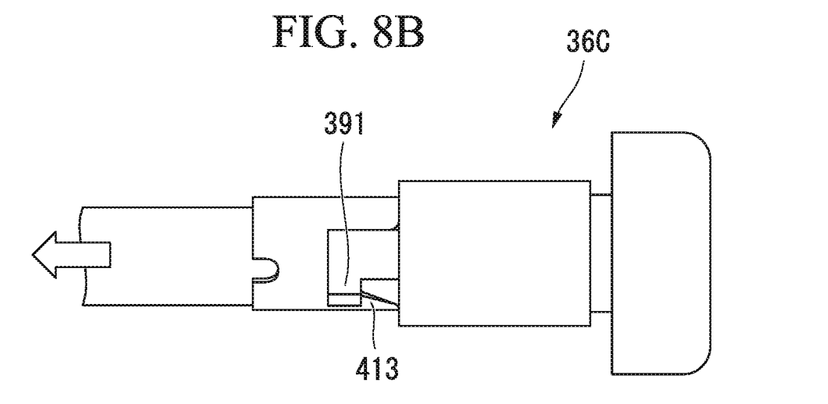
FIG. 8B is a view showing the bolt portion and the manipulation wire of the modified example of the thread fixing tool.
Figure 8C:
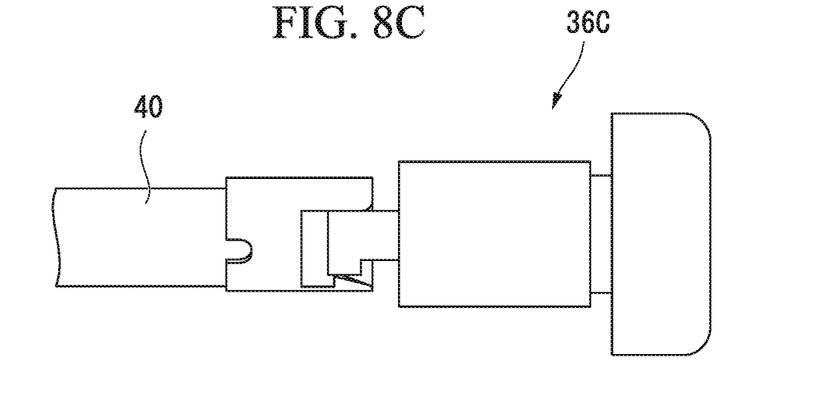
FIG. 8C is a view showing the bolt portion and the manipulation wire of the modified example of the thread fixing tool.

Another example of the coupling portion will be described in FIGS. 8A to 8C. As shown in FIG. 8A, a pawl portion 413 is provided in a notch 411B of a distal end tip 410B and an engaging portion 391 that is capable of engaging with the pawl portion 413 is provided in a wall portion 390B of a bolt portion 36C.

In an initial state shown in FIG. 8A, the manipulation wire 40 and the bolt portion 36C are coupled by engaging with the pawl portion 413 and the engaging portion 391. When the distal end tip 410B is rotated with respect to the bolt portion 36C from the initial state, as shown in FIG. 8B, an engagement between the pawl portion 413 and the engaging portion 391 come off. In this state, when the manipulation wire 40 is retracted, as shown in FIG. 8C, the manipulation wire 40 and the bolt portion 36C can be come off.

In the present modified example, if a direction in which the manipulation wire 40 rotates when approaching the bolt portion 36C to the nut portion 31 and a direction in which the manipulation wire 40 rotates when releasing the engagement between the pawl portion 413 and the engaging portion 391 are same, the pawl portion and the engaging portion may be formed so as to differ from the rotating direction of the above two procedure because it is possible to release the coupling during fixing the suture thread.

The first clamping surface and the second clamping surface may be not formed in a flat shape. FIGS. 9A to 9D are schematic diagram about another example of a shape of the second clamping surface.

As shown in FIG. 9, a plurality of fine concave-convexity portions 60 may be provided in the second clamping surface 37a. In this case, concave-convex portions 60 dig into the clamped suture thread and a friction is occurred between the suture thread and concave-convex portions, thereby the clamping suture thread can be fixed rigidly.

Figure 9A:
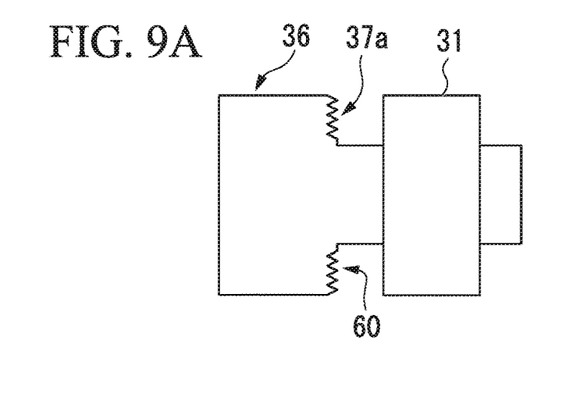
FIG. 9A is a view showing a bolt portion and a nut portion of the modified example of the thread fixing tool.
Figure 9B:
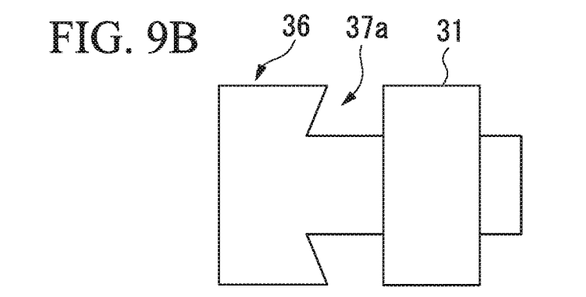
FIG. 9B is a view showing a bolt portion and a nut portion of the modified example of the thread fixing tool.
Figure 9C:
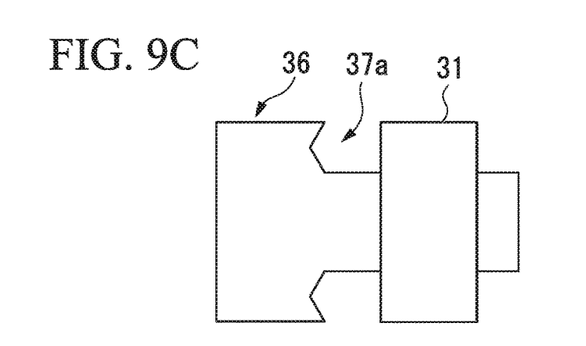
FIG. 9C is a view showing a bolt portion and a nut portion of the modified example of the thread fixing tool.

As shown in FIGS. 9B and 9C, a periphery of the second clamping surface 37a may be formed so as to protrude toward the first clamping surface. Therefore, it is difficult for the suture thread to drop from between the bolt portion 36 and the nut portion 31. As shown in the example of FIGS. 9B and 9C, in the second clamping surface 37a, even if a portion orthogonal to the axis line of the insertion portion 10 do not exist, the suture thread can be clamped and fixed suitably.

Figure 9D:
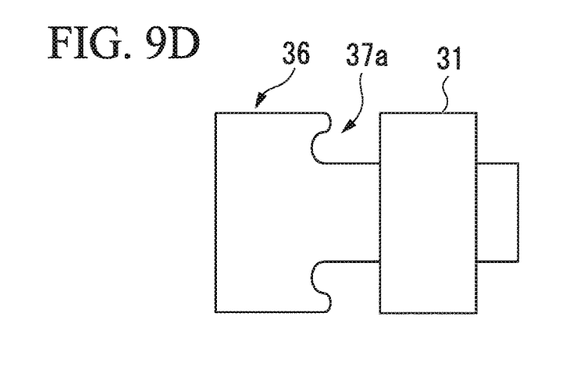
FIG. 9D is a view showing a bolt portion and a nut portion of the modified example of the thread fixing tool.

As shown in FIG. 9D, an outer surface of a periphery portion that is protruded in the second clamping surface 37a may be formed in a curved shape. A periphery of the second clamping surface may be protruded over the entire periphery, may be protruded partially, or at intervals intermittently.

FIGS. 9A to 9D are described as examples of the shape of the second clamping surface. The similar changes may be adapted for the first clamping surface, and for both clamping surfaces.

Next, a first embodiment of the present invention will be described with reference to FIG. 10.

An arrangement of the first member and the second member differs from the thread fixing tool of the present embodiment and the thread fixing tool 1 of the first embodiment.

In the embodiments to be described below, the same constituent elements as those of the above-described first embodiment will be designated by the same reference numerals, and duplicate description will be omitted.

Figure 10:
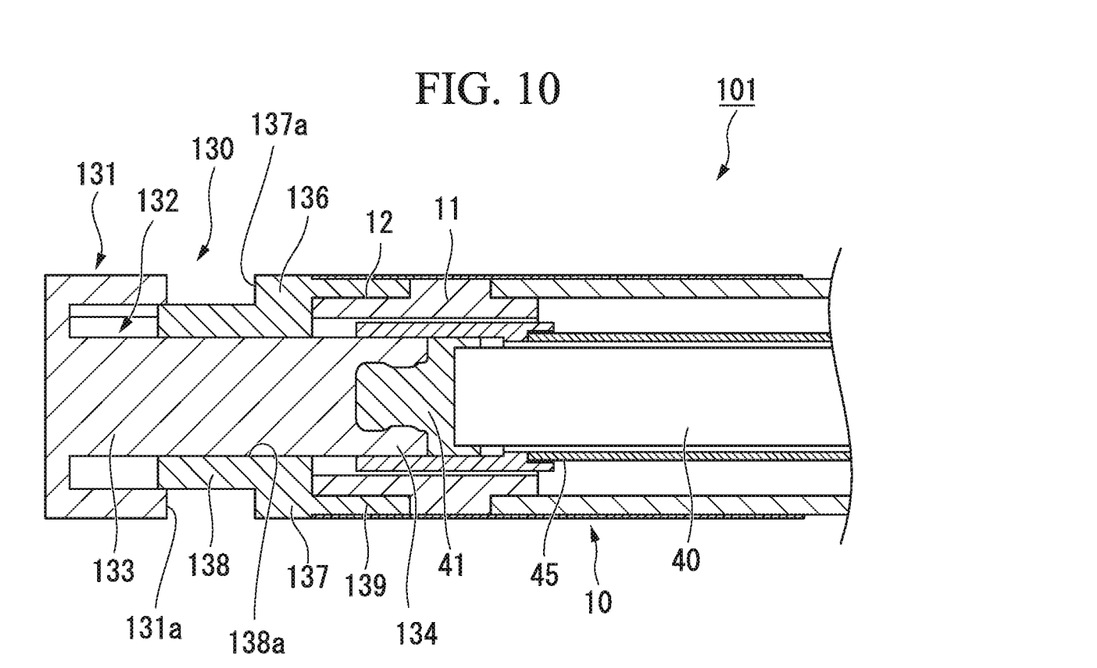
FIG. 10 is an enlarged sectional view of a distal end portion of the thread fixing tool according to a second embodiment of the present invention.

FIG. 10 is an enlarged sectional view of a distal end portion of the thread fixing tool 101 of the present embodiment. A fixing portion 130 of the thread fixing tool 101 includes the nut portion 131 and the bolt portion 136.

An engaging portion 139 is formed in a disk portion 137 of a bolt portion 136. The bolt portion is attached to a distal end of the insertion portion 10 by causing the engaging portion 139 to be entered into the engaged portion 12 in a state of directing a screw portion 138 toward a distal end side.

The nut portion 131 includes a screw hole 132 that has a bottom and a coupling axis 133 that is protruded from a bottom surface of the screw hole 132. The coupling axis 133 includes a pair of wall portions 134 at a protruded end. The coupling axis 133 enters into a hole 138a that is formed in the screw portion 138, and is coupled to the coupling chip 41 in a form similar to the screw portion 38 of the first embodiment.

In the thread fixing tool 101, by screw-fitting the nut portion 131 and the bolt portion 136, the first clamping surface 131a and the second clamping surface 137a can be caused to approach each other, and the suture thread that enters between the first clamping surface 131a and the second clamping surface 137a can be clamped and fixed.

While the preferred embodiments of the invention have been described and shown above, it should be understood that these are exemplary of the invention and are not to be considered as limiting. Additions, omissions, substitutions, and other modifications of components can be made without departing from the concept of the invention. The present invention is not limited by the description above.

For example, an end portion of the other one of the first fixing member and the second fixing member that is coupled to the manipulation member includes three or more wall portions instead of the pair of wall portions. Three or more wall portions are arranged in a circumferential direction at regular intervals, thereby the torque which is occurred by the rotation manipulation can be transmitted suitably to the other one of the first fixing member and the second fixing member that is coupled to the manipulation member.

The engaging portion of the other one of the first fixing member and the second fixing member can be similarly changed.

The rotation manipulation of the manipulation portion and the rotation manipulation of the fixing portion do not always secure synchronization. In a case where the synchronization is not secured, in a process of rotating the firs fixing member relative to the second fixing member, it is possible for one of the first fixing member and the second fixing member that is attached to the insertion portion to move relatively in the axis line direction with respect to the insertion portion. In this case, for example, it prevents one of the first fixing member and the second fixing member from coming off unintentionally from the insertion portion during clamping and fixing by sufficiently securing a length of the engagement between the engaging portion and the engaged portion.

What is claimed is:

1. A thread fixing tool comprising:
    a first fixing member which includes a screw hole and a first clamping surface;
    a second fixing member which includes a second clamping surface and screw-fits with the first fixing member;
    an insertion portion which is flexible and tubular, either one of the first fixing member and the second fixing member being attached to a distal end portion of the insertion portion;
    a manipulation wire which is inserted into the insertion portion and to which the other one of the first fixing member and the second fixing member is coupled;
    a manipulation knob which is connected to a proximal end portion of the manipulation wire; and
    a sheath which is arranged in the insertion portion and into which the manipulation wire is inserted, wherein
    the first fixing member and the second fixing member are arranged such that the first clamping surface and the second clamping surface face each other in an axis line direction of the insertion portion,
    when the insertion portion rotates relative to the manipulation wire by manipulating the manipulation knob, the first clamping surface and the second clamping surface are configured to be close to each other by screw-fitting with the first fixing member and the second fixing member,
    when a predetermined manipulation is performed to the manipulation knob, a coupling between the manipulation wire and the other one of the first fixing member and the second fixing member is configured to be released, and
    the manipulation wire and the other one of the first fixing member and the second fixing member are configured to be coupled such that the coupling is capable of being released by causing the sheath to be retracted with respect to the manipulation wire.

2. The thread fixing tool according to claim 1, one of the first fixing member and the second fixing member is attached to the insertion portion so as to be capable of moving relative to the insertion portion in the axis line direction and so as not to rotate around the axis line relative to the insertion portion.

3. The thread fixing tool according to claim 1, wherein the predetermined manipulation is a manipulation in which the manipulation wire is retracted with respect to the insertion portion.

4. The thread fixing tool according to claim 1, wherein the predetermined manipulation is a manipulation in which the manipulation wire is rotated relatively with respect to the insertion portion.

5. The thread fixing tool according to claim 1, wherein the manipulation wire and the other one of the first fixing member and the second fixing member are coupled via a fragility portion, and
    the fragility portion is configured to be broken by the predetermined manipulation.

6. The thread fixing tool according to claim 1, wherein the first clamping surface and the second clamping surface are orthogonal to an axis line of the insertion portion.

7. The thread fixing tool according to claim 1, further comprising,
    a wall which is provided in a proximal end portion of one of the first fixing member and the second fixing member, wherein
    the wall is capable of being detached from and attached to a coupling that is provided in a distal end of the manipulation wire.

8. An endoscope system, comprising:
    an endoscope which includes an insertion portion that is flexible; and
    the thread fixing tool according to claim 1 which is attached along an outer peripheral portion of the insertion portion of the endoscope, wherein
    the first fixing member and the second fixing member are protruded from a distal end side of the endoscope than a distal end of the insertion portion.

9. A method for fixing a suture thread using the thread fixing tool according to claim 1, the method comprising:
    entering the suture thread between the first fixing member and the second fixing member;
    causing the first fixing member and the second fixing member to be close to each other by screw-fitting with the second fixing member and the first fixing member, and clamping and fixing the suture thread;
    releasing the coupling by causing the sheath to be retracted with respect to the manipulation wire; and leaving the first fixing member and the second fixing member in a state of cramping and fixing the suture thread in a body.

* * * * *